United States Patent [19]

Katims

[11] Patent Number: 5,078,714

[45] Date of Patent: Jan. 7, 1992

[54] METHOD AND APPARATUS FOR PLACEMENT OF A PROBE IN THE BODY AND THE MEDICAL PROCEDURE FOR GUIDING AND LOCATING A CATHETER OR PROBE IN THE BODY

[76] Inventor: Jefferson Katims, 1082 Park Ave., New York, N.Y. 10128-1122

[21] Appl. No.: 487,303

[22] Filed: Mar. 2, 1990

[51] Int. Cl.$^5$ ............................................. A61B 17/39
[52] U.S. Cl. ...................................... 606/38; 604/95; 604/264; 604/280; 606/32
[58] Field of Search ............... 604/95, 264, 280, 282, 604/65, 66, 53, 113, 114; 606/32, 34, 35, 38, 41, 46, 50, 234

[56] References Cited

U.S. PATENT DOCUMENTS

| | | | |
|---|---|---|---|
| 4,610,705 | 7/1986 | McCoy | 604/95 |
| 4,838,859 | 6/1989 | Strassman | 604/95 |
| 4,923,165 | 1/1991 | Loiterman | 604/164 |

FOREIGN PATENT DOCUMENTS

| | | | |
|---|---|---|---|
| 1447376 | 12/1988 | U.S.S.R. | 604/280 |
| 2213381 | 8/1989 | United Kingdom | 606/38 |

Primary Examiner—John D. Yasko
Assistant Examiner—M. Mendez
Attorney, Agent, or Firm—Karl W. Flocks

[57] ABSTRACT

A method and apparatus for guiding a physician in the placement of a probe in the body. The method of placement of a catheter or probe in the body through a multi-directional walled path departing from a straight line involving inserting an insulated catheter or probe with a distal uninsulated tip which is electronically connected in a circuit to an electronic catheter guidance system apparatus located outside the patients body which has a power source and a calibrated monitor. The catheter is advanced by a physician into an initial opening in said multi-directional path in a patient's body moving the tip of said catheter or probe forward along said path until the calibrated monitor displays that an obstruction has been met indicating a change in path direction. Using this information the physician halts or discontinues or slows down in the forward movement of said catheter or probe until an adjustment is made such as by twisting or turning or externally pushing the contacting wall so that forward movement of the catheter or probe may be continued without obstruction as determined by the information provided by the electronic catheter guidance system display. The physician repeats such steps as the calibrated monitor displays that the catheter tip is within the desired walled path and that the catheter may be utilized.

8 Claims, 5 Drawing Sheets

1

METHOD AND APPARATUS FOR PLACEMENT OF A PROBE IN THE BODY AND THE MEDICAL PROCEDURE FOR GUIDING AND LOCATING A CATHETER OR PROBE IN THE BODY

Disclosure documents relating to the present invention filed with the U.S. Patent and Trademark Office:
No. 154,905 Aug. 19, 1986
No. 190,679 Feb. 2, 1988
No. 216,792 Dec. 23, 1988

FIELD OF THE INVENTION

The present invention relates to a system of assisting in the placement of a medical probe; catheter or other tubular or rod shaped medical device into the human body and guiding the movement of this device through a multi-directional walled path departing from a straight line. This catheter or probe is connected in a circuit having a power source and a calibrated monitor which continuously evaluates the impedance characteristics of the tissue at the tip of the catheter and indicates when an obstruction is met at its tip, i.e. it is against or has entered into the wall of the path along which it is being placed. This information is used to guide movements of the catheter or probe during its insertion to insure that it remains within the desired walled path, such as a blood vessel (vessel, i.e., artery or vein). This is not imaging but relates to the local environment of the catheter tip.

BACKGROUND OF THE INVENTION

When a catheter or probe is being placed in a human body, there is generally no aid in determining the path of the placement other than by intimate knowledge of the body part and by touch and feel or extraction of bodily fluid. An X-ray, sonogram or similar diagnostic device, however, is used to confirm the location of a catheter, for example, near the heart so as to rule out accidental placement into a lung, which often causes pneumothorax. The time required of such X-ray confirmation delays the use of such a central line catheter even in life threatening situations.

DESCRIPTION OF THE PRIOR ART

The remote monitoring of the electrical characteristics of the human body through percutaneously implanted electrical devices is well-known. U.S. Pat. No. 4,552,127 issued to Schiff on Nov. 12, 1985 describes such a device. Also, it is known to apply electrical signals to the human body; U.S. Pat. No. 3,664,329 issued to Naylor on May 23, 1972 describes such a device.

U.S. Pat. No. 4,651,280 issued to Chang on Mar. 17, 1987 describes an electrosurgical control system using a predetermined tissue load to control power to an electric scalpel. An output electrode, or cutting device, is connected by cable to an electrosurgical unit (ESU). A current probe is attached near the surface of the output cable of the electrosurgical unit (ESU) in order to take variations of the output current and transmit them to a microprocessor control unit (MSU) by way of a return electrode. The electrical probe transmits electrical variations on the output power of the ESU caused by variations of body tissue encountered by the cutting device to the MSU. When the MSU detects a predetermined output level of the ESU it generates an output signal which causes a relay to disconnect the power from the ESU to the electronic scalpel. The disclosure of Chang illustrates of a method of putting a circuit breaker on an electrical scalpel for a novice in the operation of a trans urethral procedure. There is no direction or specification of procedure to complete the transurethral operation by such an amateur.

Without output power to the ESU the surgical procedure may not continue to completion. The continuation of the effective transurethral operation, however, is not described by Chang and, in this sense, the disclosure is completely defective in the sense that the final result is not obtained.

The final result which is obtained by Chang is merely a withdraw of the amateurish steps taken by the operator of the ESU which in effect is similar to a situation in which an overload occurs in an electrical circuit which throws a circuit breaker into inoperative position. If the circuit breaker is again turned on it will cut itself off immediately because the breakdown or short circuit in the mechanism has not been corrected. It is necessary to make the correction before one can throw the circuit back into operation. Chang basically describes a circuit breaker.

U.S. Pat. No. 3,834,374 issued to Ensanian on Apr. 6, 1972 describes a process for diagnostic electrical scanning of the skin for changes in monitored skin electrical potentials to allow for the mapping of said potentials. U.S. Pat. No. 4,649,923 issued to Smith on Mar. 17, 1987 describes a method and apparatus for deriving the impedance of a large zone of the body composed of many different tissue types. U.S. Pat. No. 3,980,077 issued to Shaw on Sept. 14, 1976 describes a hand held resistivity meter to be applied along the skin overlying the spine of a patient to evaluate skin resistance over various locations overlying the spine of the patient for the purpose of locating acupuncture points and areas of trauma along the spine.

Prior patents describe the employment of electrical impedance methods in the medical field. They deal with the imaging of internal organs, U.S. Pat. No. 4,539,640 issued to Fry and Wexler on Sept. 3, 1985, titled "Reconstruction system and methods for impedance imaging" describes the employment of a plurality of electrical signals from an electrode array injected into a structure in time sequence or as multiplex signals through input sites located upon or within a structure, causing current flow along a plurality of paths through each region which terminate in output sites located upon or within the structure, in order to obtain an overall image of the structures located upon the entire path in which the electrical signal is traveling. Similar imaging may be obtained by a X-ray or ultra-sound.

Other references regarded relevant to the present invention are set out below:

| U.S. Pat. Nos. | Inventor(s) U.S. Patents | Issue Date |
| --- | --- | --- |
| 3,784,908 | Anderson | 01/08/74 |
| 3,789,834 | Durox | 02/05/74 |
| 3,894,532 | Morey | 07/15/75 |
| 3,971,365 | Smith | 07/27/76 |
| 4,258,724 | Balat et al. | 03/31/81 |
| 4,467,807 | Bornzin | 08/28/84 |
| 4,624,265 | Grassi | 11/25/86 |
| 4,637,404 | Gessman | 01/20/87 |

However, none of this prior art teaches a method and apparatus for evaluating impedance characteristics at the tip of a probe or catheter in order to assist in the placement of a medical probe; catheter or other tubular or rod shaped medical device into the human body and guiding the movement of this device through a multi-directional walled path departing from a straight line.

SUMMARY OF THE INVENTION

It is an object of the present invention to provide a system and a method to assist in the subcutaneous placement of a catheter or probe into the body of a patient by monitoring and evaluating the characteristic impedance of the body tissue into which the distal end of the catheter comes into contact during the placement process. The local impedance characteristics of body tissue are evaluated over the range of DC to ultra-violet. The electrical characteristics include resistance and impedance measures over the range of frequencies from DC to higher frequencies such as microwave and into optical. For the purposes of this specification all of the electromagnetic signals when not otherwise identified will be referred to as electrical signals. At higher frequencies the tissue impedance is often best viewed as absorption and reflection coefficients as a function of wavelength. This is not imaging but relates to the local environment of the probe.

A description of the present invention is to provide a system and a method to assist in the subcutaneous placement of a catheter into the body of a patient by comparative evaluation of the impedance characteristics of the body tissue into which the distal end of the catheter comes into contact during the placement process. This would assist in the placement of, for example, a standard intra-venous syringe.

In accordance with the above objects and other objects which will become apparent hereinafter, there is provided a guidance system for assisting in the subcutaneous placement of a catheter or probe to a specific site in the body of a patient. The catheter or probe will hereafter be referred to as a "catheter". The term "tissue" will be used hereafter to refer to any location within a body, this would include organs, vessels, cavity walls and arteries and veins and so forth. The term "tissue" refers to cellular components of the body. The term "fluid", as used hereinabove and hereafter, refers to non-cellular components of the body, including blood and spinal fluid. An electronic catheter contains the means which transmits electrical energy through the catheter between its proximal end which is located outside the body and the distal end which is inserted inside the body that will hereafter be referred to as a "transmission line". Additional transmission lines may also be in circuit between the skin (tissue) of the subjects body and the electrical guidance system. All transmission lines are insulated from transmitting electrical signals to the body tissue which they contact except at their distal ends. This site will hereafter be referred to as the "transmission contact area". The transmission line may be as simple as a conductor at D.C. and low frequencies or as complex as a dielectric wave guide for use in higher frequencies such as optical. Additionally, this transmission line for may be composed of a fluid within a tube within a catheter; for example, an electrolyte containing solution may be used as a conductor at D.C. and low frequencies, whereas as dielectric solution of appropriate dielectric constant to enable the absorption and transmission of the desired higher frequencies may be used to serve as a dielectric wave guide. Alternatively, a conventional fibre optic cable may serve as the transmission line.

For the purpose of this specification, resistance is defined as the subset of impedance relating to the impedance at D.C. The process of monitoring the impedance of body tissue at low frequencies consists of forcing a known voltage across or current through the tissue and. measuring the resulting current or voltage respectively. The impedance is defined as a complex ratio of voltage divided by current.

In the simplest case at low frequencies, the electronic catheter guidance system, employing a catheter with only a single transmission line must also employ a transmission line which is in electrical connection with the body of the patient. This additional transmission line is not strictly required when an electronic catheter is employed which has more than one transmission line. The electrical guidance system continuously monitors the electrical signals relating to impedances of body tissue between the two transmission contact areas as the catheter is moved through the body of the patient and the catheter tip transmission contact area comes into contact with body tissue. An electrical signal sent to a catheter transmission line passes between this line's transmission contact area located at the catheter tip through body tissue to the other transmission lines transmission contact area and the return transmission contact area.

At higher frequencies such as microwave and optical, the electrical catheter guidance system may employ only a single transmission line within the electrical catheter to evaluate the absorption and reflection coefficients and determine the impedance characteristics of the tissue located at the catheter tip.

Furthermore, at low electrical frequencies, this method may also be employed with standard multi-lumen (lumen, i.e., passage within a tube) catheters by electrically monitoring from the external catheter ports of lumens filled with an electrolyte containing solution (e.g. blood or saline). An electrolyte filled lumen within a catheter, enables such an application i.e., by serving as an electrical conducting medium within the lumen conducting between its opening at the catheter tip and its external port. This enables the catheter tip opening to function as a local electrode, and the catheter itself serves as the insulator of this electrode. These tip located electrodes allow the monitoring of the electrical properties of the tissue into which the tip contacts. This provides practical catheter placement guidance information to the practitioner by indicating whether while inserting a needle/catheter it remains located within the same multi-directional walled path. For example while placing a needle within a walled path such as a vein that is filled with blood the impedance characteristics monitored from the tip of the catheter will indicate on a calibrated monitor guidance system that the tip is in blood. If, however, during the placement procedure the tip of the catheter touches against the wall of the vein, the catheter guidance system will alert the individual placing the catheter as to this condition, and to stop advancing the placement of the catheter and start its slow withdrawal and change direction. As soon as the withdrawing catheter tip moves away from the wall of the vein and is surrounded again by the blood located within the vein, the catheter guidance system monitor will alert the individual placing the catheter as to this condition (i.e. that the catheter tip is surrounded by blood). The monitor will then indicate to stop withdrawing the catheter and continue its insertion placement again with an adjustment such as twisting or turning the catheter or externally pushing the contacting wall so that forward movement of the catheter may be continued without obstruction. Such steps are repeated until the calibrated monitor displays desired location has been reached whereby the indicated treatment may be administered such as, for example, feeding (supplying, administering) a drug or a food substance for alleviating pain or supplying energy or normalizing an abnormal condition.

This catheter guidance system obtaining the electrical characteristics of living tissue located at the tip of the catheter enables the guidance of the catheter through a multi-directional walled path departing from a straight line within a body, and is part of the invention of this present disclosure.

The present invention for catheter guidance has an application in the practice of anesthesia for the administration of a spinal anesthetic (i.e. just outside the spinal cord). Presently an anesthesiologist relies upon the feel of the placement of a catheter or the ability to extract cerebral spinal fluid to confirm the placement of a catheter just outside the spinal cord in the intrathecal space. This space is the most superficial surface of the spinal cord and is filled with spinal fluid. The most serious and common complication is spinal anesthesiology today is the accidental administration of an anesthetic directly into the spinal cord. Such a mistake is a major complication of spinal anesthesia and often leads to permanent paralysis of the patient of those regions of the body innervated by regions of the spinal cord below the site of administration of the anesthetic (usually permanent paralysis of the lower extremities). In the present invention, by monitoring the electrical impedance characteristics at the tip of the catheter used for spinal anesthesia, the impedance characteristics of the tissue at the tip of the probe may be continuously monitored to insure that the probe tip is located within the multi-directional walled path departing from a straight line with the inside wall being the spinal cord and the outside wall being the dura mater covering the spinal cord, i.e. within the intra thecal space that is normally filled with spinal fluid or within a median with similar impedance characteristics. If the probe tip should accidentally touch the spinal cord the monitored impedance should increase by approximately 30 fold and inform the anesthesiologist not to inject the anesthetic agent at the present position of the catheter tip because it is positioned dangerously for such an action. The anesthesiologist would then withdraw the catheter slightly until the catheter tip monitored electrical characteristics indicated that it was located in tissue with the characteristic impedance of spinal fluid, indicating a safe condition for the administration of an anesthetic agent, thereby preventing catastrophic damage to the patient. Furthermore the monitored electrical characteristics from the catheter guidance system may be recorded for documentation of the procedure.

Impedance measures have been taken on the body for imaging and the like, such as, for example, the method of impedance imaging in the U.S. Pat. No. 4,539,640 issued to Fry and Wexler. The present invention is distinguished from this and differs by utilization of impedance measures not for imaging but qualitative analysis of the tissue at tip of the catheter. The present invention makes use of this qualitative impedance analysis in an advantageous way to get results which are safer, more facile and less expensive than current procedures in medicine. The application of the present invention assists in guiding the medical practitioner in the placement of a catheter or other tubular or rod shaped medical device into the human body and guiding the movement of this device through a multi-directional walled path departing from a straight line, and allowing for therapeutic intervention.

The present invention will be better understood and the objects and important features, other than those specifically set forth above, will become apparent when consideration is given to the following details and description, which when taken in conjunction with the annexed drawings, describes, discloses, illustrates, and shows preferred embodiments or modifications of the present invention and what is presently considered and believed to be the best mode of practice in the principles thereof. Other embodiments or modifications may be suggested to those having the benefit of the teachings herein, and such other embodiments or modifications are intended to be reserved especially as they fall within the scope and spirit of the subjoined claims.

DETAILED DESCRIPTION OF THE PREFERRED EMBODIMENTS

Figure 1:
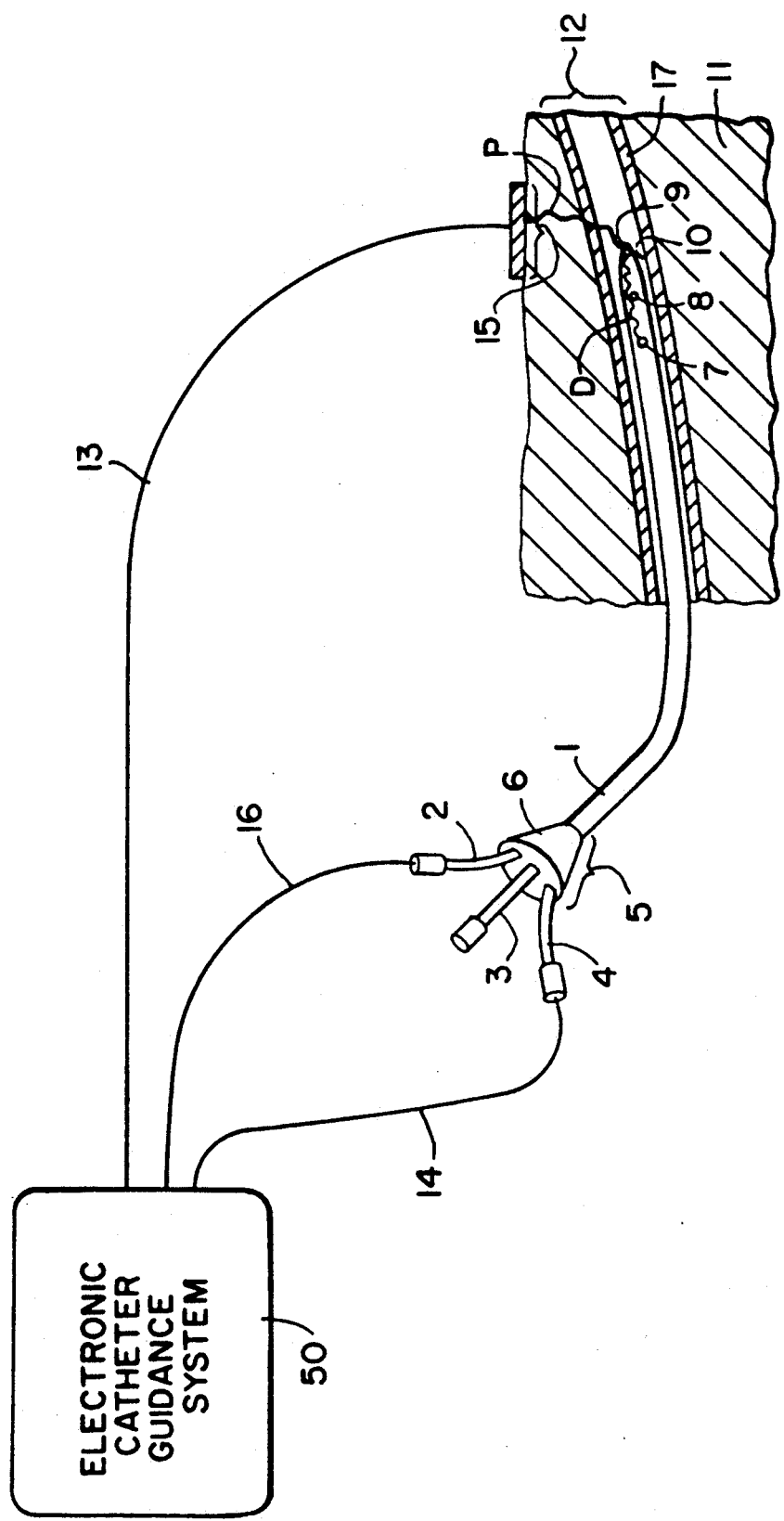
FIG. 1 is a schematic drawing of a catheter electronic guidance system including a catheter having three lumens that are each capable of passing fluid to the body of the patient. Two transmission lines are positioned in two different lumens of the catheter terminating at the catheter distal tip at two different locations. The catheter is in the process of being inserted into a vein of a patient, a third transmission line is in contact with the skin of the patient, and the electronic guidance apparatus is operatively connected with the transmission lines.

Reference is now made specifically to the drawings in which identical or similar parts are designated by the same reference numerals throughout.

FIG. 1 illustrates a electronic catheter guidance system 50. Electronic catheter 1 having three lumens, lumens 2 and 3 and distal lumen 4 positioned within the tubular interior of catheter 1 and extending from the proximal end 5 of catheter 1 where a mounting tie 6 can if desired be used to grip lumens 2, 3, 4. Lumens 2, 3, and 4 are capable of passing lumen fluid to the body of the patient. Catheter 1, which is configured as a tubular member having generally flexible walls made of a non-electrically conductive bio-compatible material such as plastic defines side openings 7, 8, which open at the side wall of catheter 1 spaced apart at catheter distal end 10, and distal opening 9, which opens at the distal tip 10 of catheter 1. Lumens 2 and 3 extend to and open coextensive with side openings 7 and 8, respectively, and lumen 4 extends to and opens coextensive with distal opening 9.

FIG. 1 illustrates the electronic catheter guidance system 50 for assisting in guiding the placement of a medical device into the body 11 of a patient within a multidirectional walled path of a blood vessel 13 to a specific site.

Electronic catheter guidance system 50 includes an electrical signal generator and may include an analog digital converter, and a switching matrix. The electronic catheter monitoring system 50 may include a computer and may have a printer or a video monitor or an audio speaker. Electronic catheter guidance system 50 is in circuit with electronic catheter 1 in the process of being inserted into a blood vessel 13. A transmission line 13 extends external to the skin of body 11 to be attached anywhere on the body with transmission contact area located at 15. Transmission line 14 passes through lumen 4 to distal end 10 of catheter 1 and ends with its transmission contact area located at opening 9. Transmission line 16 passes through lumen 2 to distal end 10 of catheter 1 and end with its transmission contact area located at opening 7. The electronic catheter guidance system 50 monitors the impedance characteristics of body tissue encountered between transmission contact area located at 9 and transmission contact area located at 7 and/or the transmission contact area located at 15.

The electronic catheter guidance system 50 which is in circuit with the electrical catheter 1 includes an electrical signal generator with an optional analog/digital converter. The electronic catheter guidance system 50 may be manually operated or it may be computerized, and may have a print out or a video monitor. Electrical monitors may include such specialized equipment as electrical, microwave or optical impedance analyzers or a custom designed electric characteristic monitor. It can be a standard multi-meter which indicates voltage, current, or impedance; or a standard oscilloscope. The electronic catheter guidance system 50 may include a voltage meter which can measure in both the time and frequency domain. It may include filters if necessary.

The electronic catheter guidance system 50 which is in circuit with the electrical catheter 1 includes an electrical signal generator and an optional analog/digital converter as well as an optional switching matrix. This device may also include a computer to allow for the programming of its functioning. The various components may be manually operated or alternatively they may be controlled by each other or the computer component. They are described as follows:

The electrical signal generator output signals transmit to the other components of the electronic catheter guidance system 50 as well as to the various transmission lines in contact with the body tissues. Depending upon its application, it is capable of generating various intensity electrical signals over the frequency range from D.C. to ultra-violet.

The analog digital converter (optional) functions in the conversion of monitored analog electrical signals into digital signals and as such includes a required filtering system. Such digital signals may be converted into alpha/numeric messages to be displayed by the electronic catheter guidance system 50.

The optional switching matrix component of the electronic catheter guidance system 50 may electronically or mechanically switch the connections between this system and the various transmission lines.

The electronic catheter guidance system 50 may be portable and battery operated.

The electronic catheter guidance system 50 monitors electrical signals transmitted through the transmission lines so that the monitored signals can be isolated. Thus, the operator has the option of isolating the monitored signals either by way of filters in electronic catheter guidance system 50 if desired, with or without utilization of electrical output signals from the electronic catheter guidance system 50.

For the monitoring of electric signals a minimum of two components of the electronic catheter guidance system 50 is required, the electrical catheter 1, one or more transmission lines depending upon the guidance system 50 output frequency.

An application of the electronic catheter guidance system 50 is to monitor and characterize the electrical characteristics of body tissue located between at least two transmission line transmission contact areas, where one of these transmission contact areas 9 is located at the tip 10 of the electrical catheter 1. One type of characterization of this tissue by the system 50 includes electrical impedance determination. The electronic catheter guidance system 50 may generate high frequency electrical signals such as micro and optical waves. This allows this system as illustrated in FIG. 1 to monitor and evaluate absorption and reflection coefficients of the tissue between one or more transmission contact areas and determine the impedance of this tissue. Transmission lines (as described) appropriate for the various types of desired electrical, microwave, or optical electrical frequencies are employed.

The following is a description of the application of the present invention when employed for the monitoring and/or evaluation of low frequency electrical signals:

Electronic catheter guidance system 50 when generating a low frequency electrical signal output to the desired transmission lines provides a controlled current or voltage with the compliance limits placed upon the uncontrolled parameters within the bounds defined by it signal generator. The means of controlling the current or the voltage may be manual, automatic or with a computer.

The monitored signal may be displayed and an instructional signal may also be from electronic catheter guidance system 50. The output current from the electronic catheter guidance system 50 may be either direct current or alternating current, which is directed to transmission line 14. From the transmission contact area of transmission line 14 located at 9 the signal passes through the body to another transmission contact area located at 15 and/or 7 to direct the current to transmission lines 13 and 16 respectively. The transmission lines 13, 14 an 16 transmit electrical signals between their tissue contact areas 15, 9 and 7 to the electronic catheter guidance system 50. The monitored analogue signals may pass through an optional analog to digital converter within the electronic catheter guidance system 50 to be converted into a digital to allow for computer analysis and/or alpha/numeric messages for display. The impedance of the body tissue between transmission contact area 9 and transmission contact area 15 or transmission contact area 7 as the catheter end 10 is moved through blood vessel 12 can be determined by many methods the easiest of which are: force a constant AC or DC current and measure the developed voltage between transmission contact area 9 and transmission contact area 15 (path P) or transmission contact area 7 (path D). The impedance, if the forced current is AC, or the resistance if the forced current is DC may calculated by dividing the measured voltage by the known forced current. Conversely, a known voltage can be forced, the developed current monitored and the impedance or resistance can be calculated by dividing the known voltage by the measured current. Alternately, a poorly controlled power source can be used in the electronic catheter guidance system 50 and both the current and voltage monitored. Again the resistance or impedance can be calculated by dividing the measured voltage by the measured current. Continuous values of voltage or current can be displayed by the electronic catheter guidance system 50 so that impedance being encountered during the electrical catheter 1 insertion process can be measured or implied. Electronic catheter guidance system 50 evaluates the monitored signal and uses its knowledge of the generated signal to continuously compute the impedance of the tissue between the various transmission contact area's as the electrical catheter 1 is moved through body 11 or blood vessel 12.

If, for example, distal tip 10 as illustrated in FIG. 1 pierces through or comes into contact with the wall 17 of the blood vessel 12, the transmission contact area of transmission line 14 located at 9 will enter into contact with the dense connective tissue of the blood vessel wall 17 and no longer remain in contact with the blood which fills the blood vessel 12. as the transmission contact area located at 9 looses it contact with the blood and enters into contact with the vessel wall 17 there will be a significant change in the monitored impedance from this transmission contact area as indicated by the electronic catheter guidance system 50 output display.

The electrical characteristics of the body tissue being calculated and monitored may continuously change in accordance with the movement of the catheter 1 and as a result the absolute electrical characteristics, that is, the absolute impedance, or measured electrical signal of the tissue between the transmission contact area located at 9 and transmission contact areas located at 7 and/or 15 will change. Both the absolute and relative values of the monitored electrical characteristics are of significance to the present invention. This is true because the total impedances measured through the body tissue 11 may be of significance primarily as relative values, that is, whether or not the resistance or impedance suddenly rises or falls. A sudden impedance increase could indicate that the transmission contact area located at 9, for example, has come into contact with the blood vessel wall 17. Another sudden return to the previous impedance thereafter associated with a movement of the electrical catheter 1 would indicate that distal tip 10 of the is no longer in the blood vessel wall and has returned to the blood vessel 12.

The electrical path of the current taken through the body 11 between the transmission contact areas located at 9 and 15 or 7 is not a straight line path but is a varied path of least electrical impedance, schematically indicated in FIG. 1 by electrical paths P and D respectively. Paths P and D tend to bypass body tissue of high impedance, such as bone and tendon, for body tissue of lower impedance. Nevertheless, comparative, or relative, values of impedance between transmission contact areas located at 9 and 15 or 7 displayed by the electronic catheter guidance system 50 will signal conditions to either go-ahead, caution, re-position or stop to the physician to assist in the placement of the electrical catheter 1. That is, the physician will make decisions based on values of impedance being currently displayed by the electronic catheter guidance system 50 or heard from its speaker as absolute values or relative values just prior to the currently displayed or played values. Although the electrical characteristics of the body tissue or both are actually measured between the various transmission contact areas 7, 9, and 15 in FIG. 1, nonetheless any significant changes in the electrical characteristics being displayed by the electronic catheter guidance system 50 are the result of local electrical characteristics of body tissue encountered at the transmission contact area located at 9. This is possible, for example when monitoring or evaluating electrical impedance characteristics with D.C. to A.C. electrical signals, by employing two different size transmission contact areas or by the positioning of transmission contact areas, for example, 9 (in blood) and 15 (on skin) such that there is a significant difference in their electrical resistances or impedances. The law of averages enables the higher resistance to dominate over the lower resistance. For example, where the first transmission line contact area measures 5 cm×5 cm (25 cm$^2$) and is located on the skin of the chest and the second transmission line contact area measures 0.05 cm$^2$ and is located at the tip of an insulated hypodermic syringe needle in a vein, the second conductor has a significantly higher resistance than the first. The impedance of the tissue located at the tip of the needle will be the dominant impedance that can be measured by the electrical catheter guidance system 50 in this example.

Figure 2A:
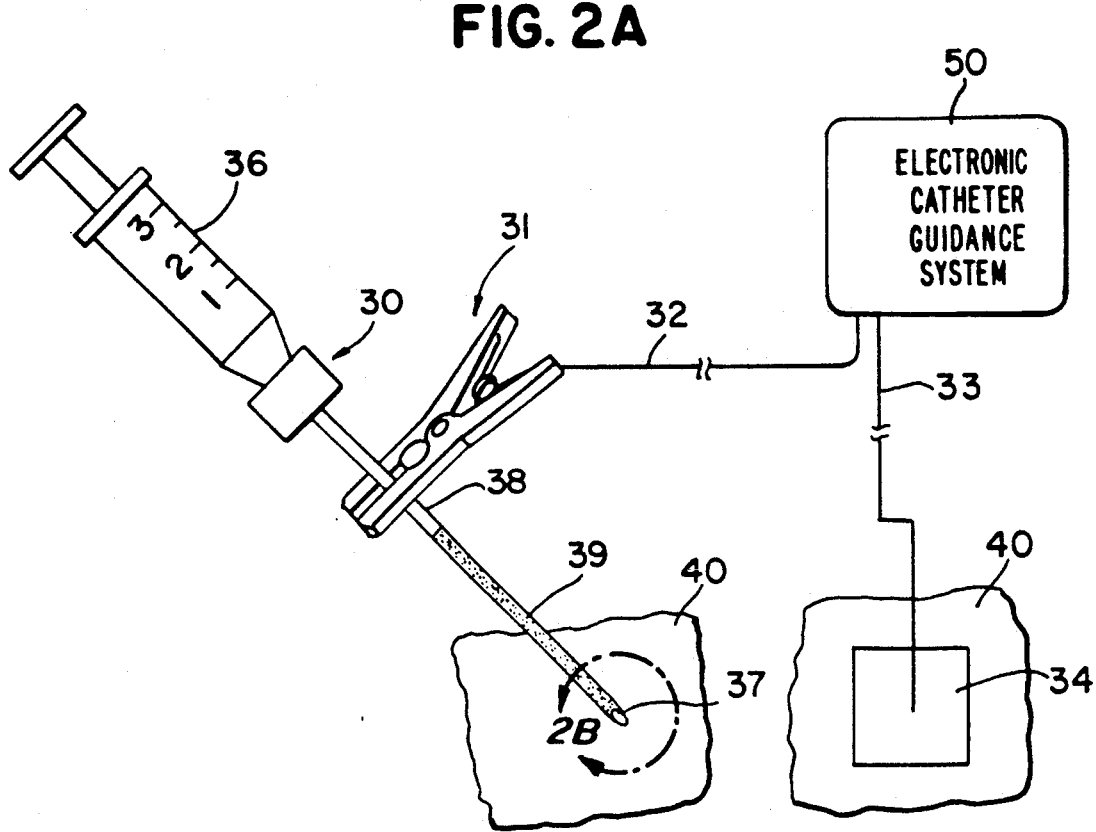
FIG. 2A illustrates an electrical catheter guidance system as may be applied for standard syringe needle for applications, using only one conductor in the needle.
Figure 2B:
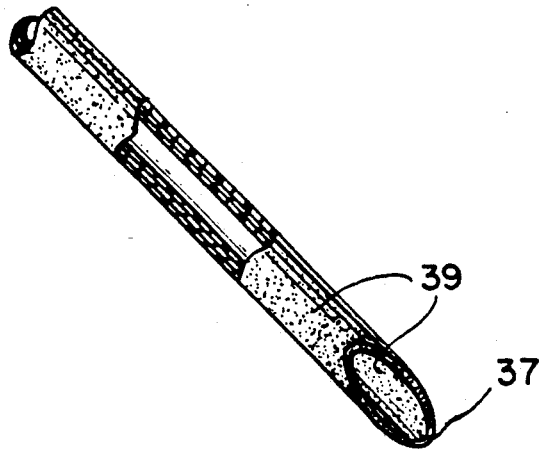
FIG. 2B is an enlargement of the needle tip in FIG. 2A.

FIG. 2A illustrates electrical catheter guidance system 50 as may be applied for standard hypodermic syringe 36 application when monitoring evaluating low frequency electrical impedance characteristics of tissue located between transmission contact area at the conductive patch 34 on the skin 40 and the transmission contact area located at the uninsulated needle tip 37 inserted underneath the skin 40. In this application the metal syringe needle 30 is electrically insulated on both the inside and the outside surfaces 39 with a bio-compatible material such as TEFLON ® except along the proximal outside surface 38 and at the tip of the needle 37. The uninsulated needle tip 37 is illustrated in FIG. 2B which is a blow-up of the needle 30 tip boxed in FIG. 2A. The metal needle 30 may serve as the conductor between these two uninsulated areas, 38 and 37. An electrically conductive clip 31 which is connected by an appropriate transmission line 32 to the electronic catheter guidance system 50. The electronic catheter guidance system 50 is analogous to the electronic catheter guidance system 50 described in FIG. 1. Another transmission line 33 attached to the electrical catheter guidance system is attached to the subject using a conductive skin patch 34. Conductive skin patch 34 serves as a transmission contact area for transmission line 33 and uninsulated needle tip 37 serves as a transmission contact area for transmission line 32.

Figure 3:
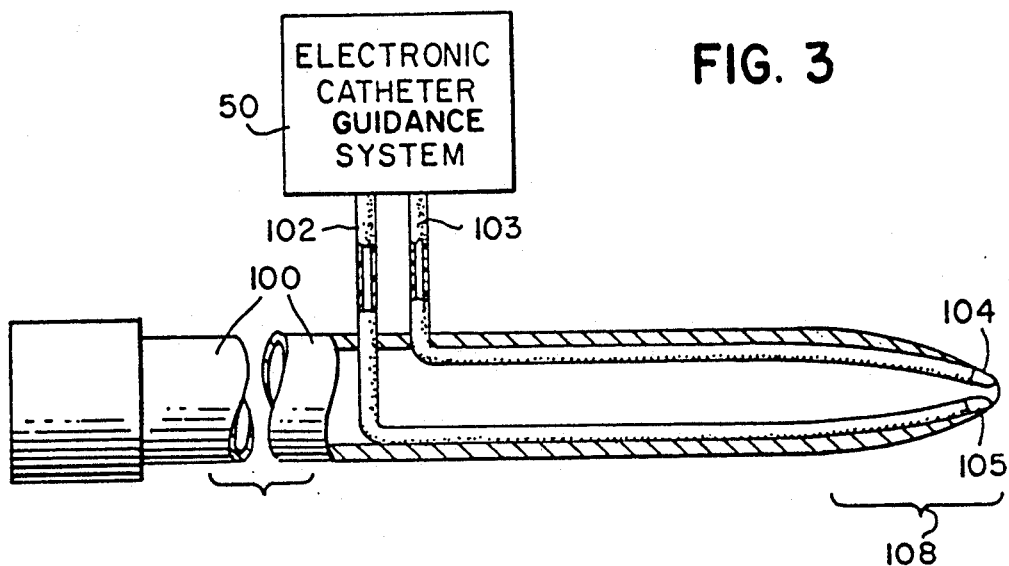
FIG. 3 illustrates electrical catheter guidance system as may be applied for standard syringe needle application, using more than one conductor in the needle.

FIG. 3 illustrates electrical catheter guidance system 50 as may be applied for standard syringe application. In this application the metal syringe needle 100 serves as the electrical catheter. The needle 1 has two insulated transmission lines 102 and 103 that course along its length. The proximal ends of transmission lines 102 and 103 are connected with the electronic catheter guidance system 50. The electronic catheter guidance system 50 is analogous to the electronic catheter guidance system 50 described in FIG. 1. The distal ends of the transmission lines are uninsulated and are located at the tip 108 of the needle 100. The uninsulated end 104 of transmission line 103 serves as the transmission contact area for transmission line 103. The uninsulated end 105 of transmission line 102 serves as the transmission contact area for transmission line 102. The electronic catheter needle 100 is configured with transmission lines 102 and 103 to permit the electronic catheter guidance system 50 to monitor and evaluate the electric characteristics of tissue in contact with transmission contact areas 104 and 105 as the needle 100 is inserted into tissue.

Figure 4A:
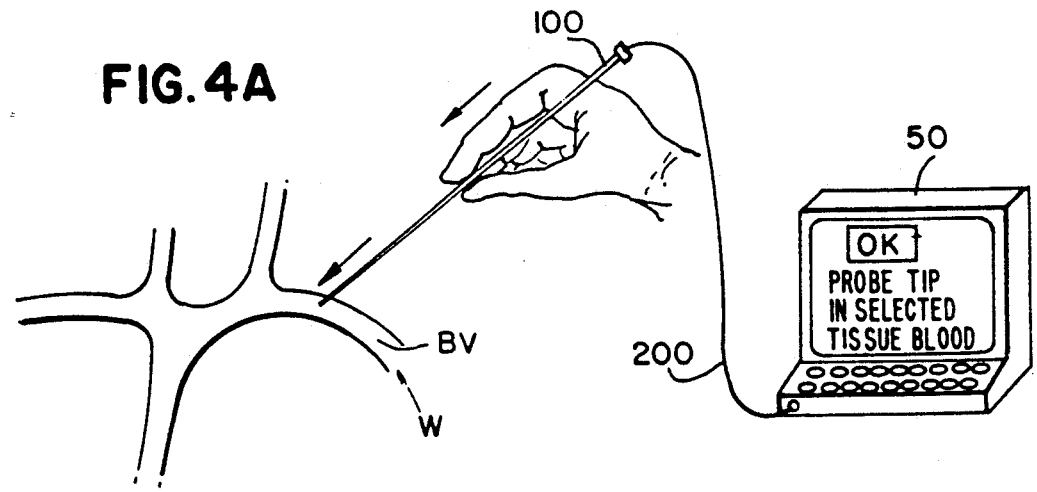
FIGS. 4A, 4B, 4C, 4D, 4E, 4F, 4G, and 4H illustrate electrical catheter guidance system as may be clinically applied as guiding the placement of a probe within a vein.
Figure 4B:
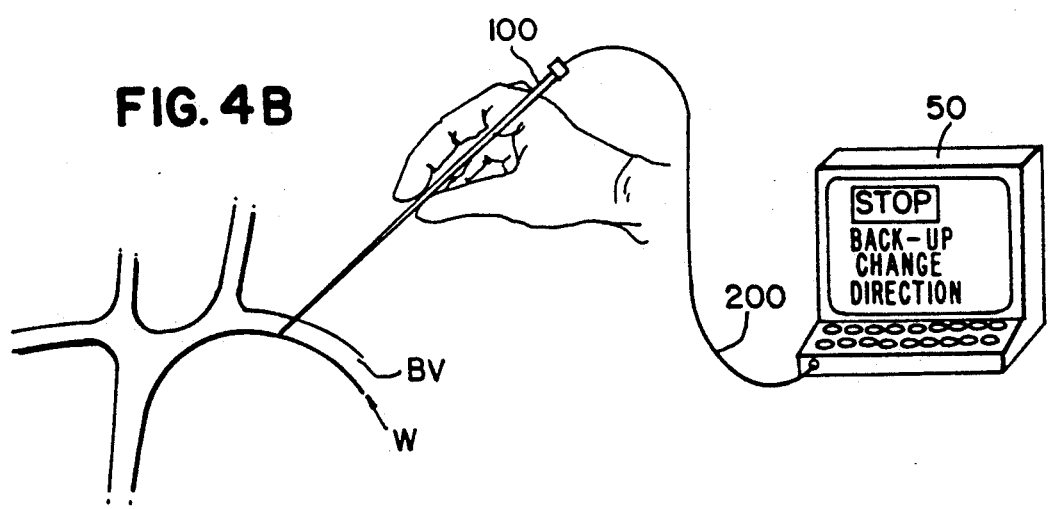

FIGS. 4A-4H illustrate electrical catheter guidance system as may be clinically applied for guiding the placement of a catheter 100 within a blood vessel BV. In this application practitioner desires to place the catheter 100 tip several centimeters into the length of a blood vessel. This catheter 100 placement location several centimeters within the blood vessel BV is medically desired to prevent the catheter 100 from slipping out of the blood vessel BV as it may if it were placed at a shorter distance within the blood vessel, for example, 0.25 centimeters. The catheter 100 is of similar design to catheter 100 in FIG. 3. Catheter 100 has two transmission lines which are located within cable 200 connected in an electronic catheter guidance system 50. The practitioner sets the electronic catheter guidance system 50 for guiding the catheter inside a blood vessel filled with blood. In FIG. 4A, the practitioners hand has pushed the catheter 100 tip into the blood vessel BV and the display on the electronic catheter guidance system 50 displays "OK PROBE TIP IN SELECTED TISSUE BLOOD". As the practitioner's hand continues to advance the catheter 100 into the blood vessel BV the tip of the catheter touches the wall W of the blood vessel BV as illustrated in FIG. 4B. Simultaneously with the tip of the catheter touching the wall of the blood vessel the display on the electronic catheter guidance system 50 will display "STOP BACK-UP CHANGE DIRECTION". The electronic catheter guidance system 50 will be able to perform this function by recognizing through an analysis of the monitored impedance characteristics from the tip of the catheter 100 that the catheter tip is no longer in the selected tissue-blood.

Figure 4C:
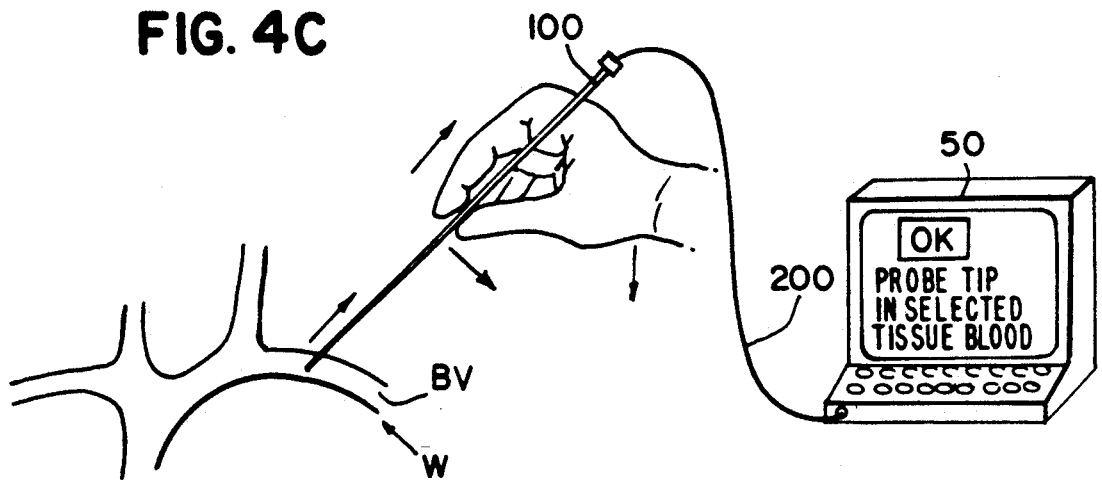
Figure 4D:
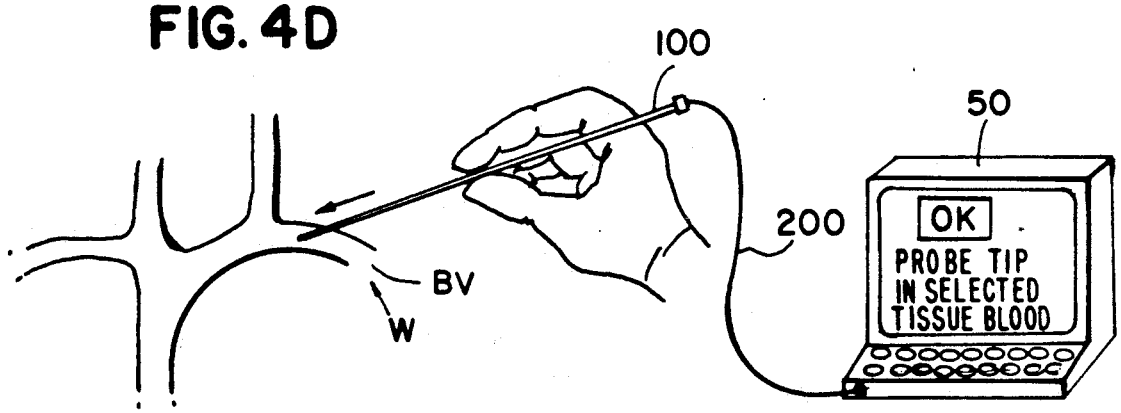
Figure 4E:
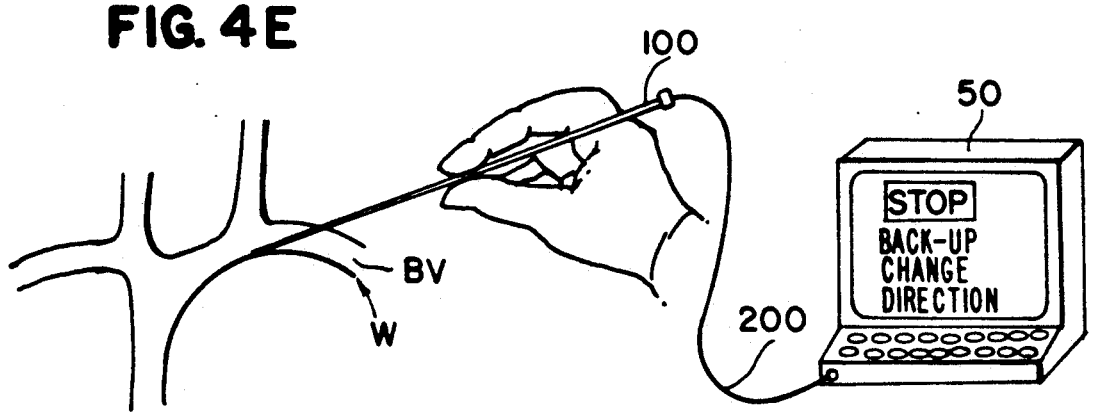

Alternatively, the electronic catheter guidance system 50 may perform this function by recognizing through a comparison with previously obtained impedance values (from the location of the tip in FIG. A) that the monitored impedance characteristics from the tip of the catheter 100 that the catheter tip in FIG. 4B is no longer in the same tissue as in FIG. 4A (blood) but is instead within or touching a different tissue (blood vessel wall) which has significantly different impedance characteristics. In FIG. 4C the practitioners hand backs up and changes the direction of the movement of the catheter 100. As soon as this reversed movement is sufficient enough to remove the tip of the catheter 100 from its contact with the blood vessel BV wall W the electronic catheter guidance system 50, after an analysis of the monitored impedance values from the tip of the catheter 100, will display the following: "OK PROBE TIP IN SELECTED TISSUE BLOOD". Once this "OK" condition as indicated by the electronic catheter guidance system 50 is signaled, the practitioner may advance the catheter 100 into the blood vessel as illustrated in FIG. 4D. As long as the electronic catheter guidance system 50 continues to display that the condition is "OK" the practitioner may continue to advance the catheter 100 several centimeters into the vein with the knowledge that the catheter tip is located within the vein until the desired final location is reached. In FIG. 4E the tip of the catheter 100 after being further advanced within the blood vessel BV (from its previous position in FIG. 4D) again touches the vessel wall W. Again, simultaneously with the tip of the catheter touching the wall of the blood vessel the display on the electronic catheter guidance system 50 will display "STOP BACK-UP CHANGE DIRECTION".

Figure 4F:
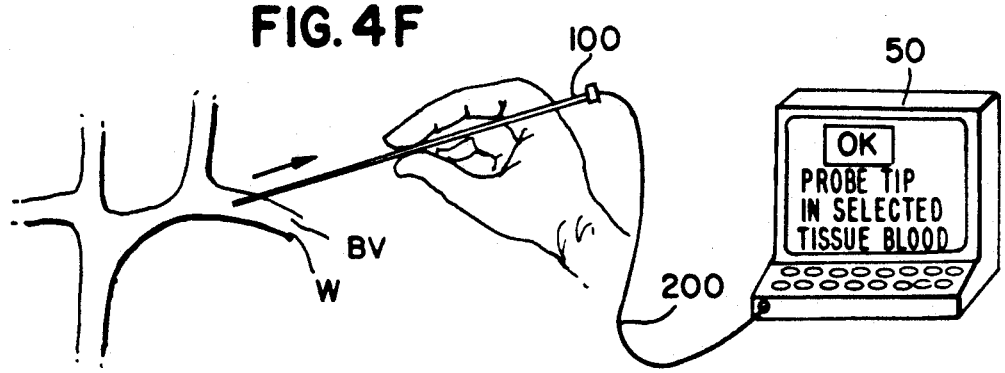

In FIG. 4F the practitioners hand backs up and but does not change the direction of the movement of the catheter 100. As soon as this reversed movement is sufficient enough to remove the tip of the catheter 100 from its contact with the blood vessel BV wall W the electronic catheter guidance system 50, after an analysis of the monitored impedance values from the tip of the catheter 100, will display the following: "OK PROBE TIP IN SELECTED TISSUE BLOOD". Once this "OK" condition as indicated by the electronic catheter guidance system 50 is signaled, the practitioner then applies the index finger of his free (left) hand on the body overlying the portion of the blood vessel BV beyond the tip of the electronic catheter as illustrated in FIG. 4F. The practitioner is able to perform this manual task with his left hand based upon his previously learned knowledge of what is recognized to be the normal anatomy of this vessel. The practitioner applies pressure with his left index finger over the distal portion of the blood vessel BV in order to move the blood vessel BV to a desired position that will allow for the advancement of the electronic catheter 100 in FIGS. 4G and 4H in the same direction as illustrated in FIG. 4D without pushing the tip of the catheter into the wall W of the blood vessel BV.

Figure 4G:
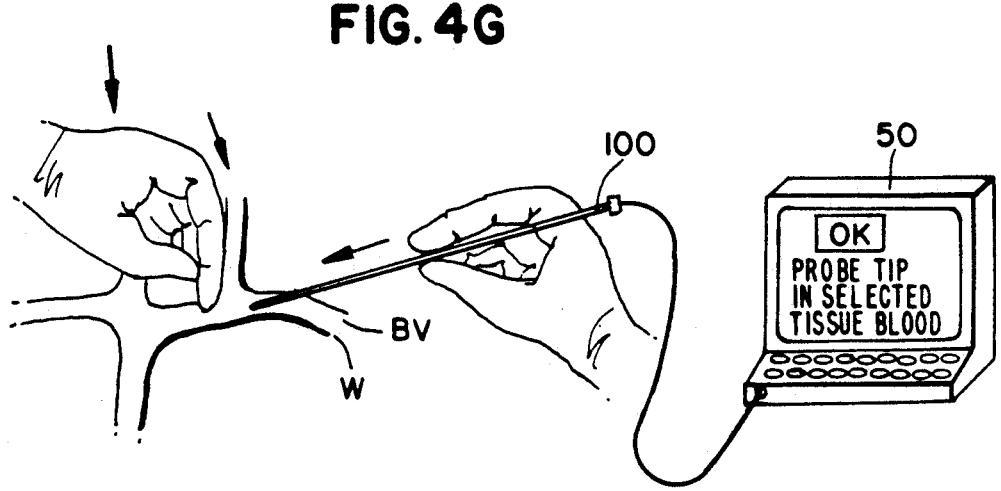
Figure 4H:
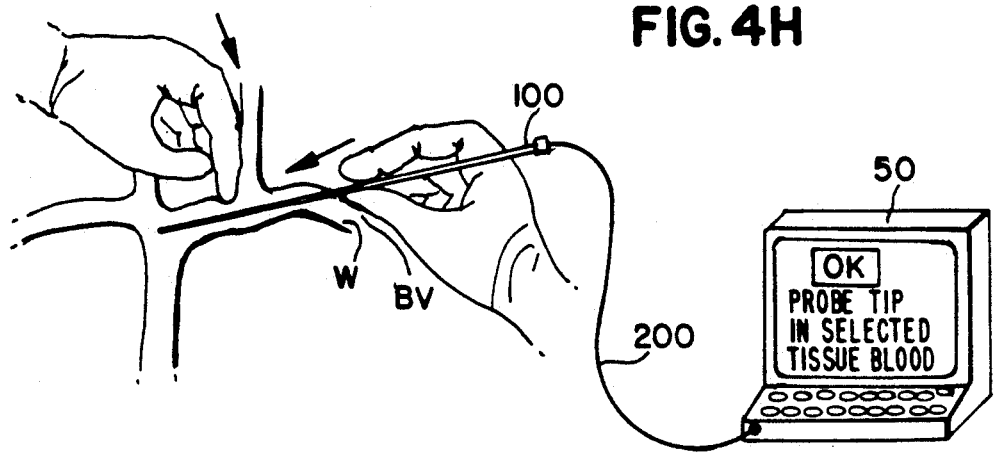

While advancing the catheter within the vessel in FIGS. 4G and 4H the electronic catheter guidance system 50 display will continuously show the practitioner that the tip of the electronic catheter 100 is in the selected tissue, which in the case is the blood located within the blood vessel BV. FIG. 4H illustrates the electronic catheter 100 being advanced to a desired distance and final location within the blood vessel BV.

Although the present invention has been described in some detail by way of illustration and example for purposes of clarity and understanding, it will, of course, be understood that various changes and modifications may be made with the form, details, and arrangements of the parts without departing from the scope of the invention as set forth in the following claims.

What is claimed is:

1. The method of placement of a tubular catheter device having an opening at its proximal end for feeding treatment fluid or withdrawing fluid and an opening at its distal end for discharging treatment fluid or receiving fluid, which distal end is also for probing a body cavity or blood vessel in the body through a multi-directional walled path having a direction which departs from a straight line, involving inserting said catheter device which has previously been connected in an electrical circuit having an electric power source and a calibrated monitor, into an initial opening in said multi-directional path, the step of moving the distal end of said catheter device forwardly along said path until the calibrated monitor displays that an obstruction has been met indicating a change in path direction, the step of halting or discontinuing or slowing down in the forward movement of said catheter device until an adjustment step is made by twisting or turning or externally pushing the contacting wall so that the step of forward movement of the catheter device may be continued without obstruction and repeating such steps until the calibrated monitor displays that the distal end of the catheter device is within the desired walled path and may be utilized for treatment by feeding or withdrawing fluid.

2. The method of claim 1 wherein the treatment is the administration of a drug.

3. The method of claim 1 wherein the treatment is the feeding of a nutrient.

4. The method of claim 1 wherein the treatment is the administration withdraw of a substance from the body through a lumen within the catheter.

5. The method of claim 2 wherein the drug is a spinal anesthetic administered just outside the spinal cord.

6. Apparatus for the placement of a tubular catheter device in the body through a multi-directional walled path which path departs from a straight line, comprising an electrical circuit, a tubular catheter device having and having an insulated distal probing end, said electrical circuit including conductor means, an electrical signal generator, and a calibrated monitor calibrated to display or register electrical impedance characteristics of various cellular tissue components of the body and fluid non-cellular components of the body characteristics in values corresponding to signals applied by said electrical signal generator whereby guided movement of said tubular catheter device in and through said path facilitates the placement of the distal end of said tubular catheter device in a desired location for administration of fluids or drugs through the proximal end of said device or withdraw of fluids through the distal end of said device corresponding to efficacious medical treatment.

7. The apparatus as recited in claim 6, wherein the tubular catheter device incorporates a series of lumens forming individual and discrete passage ways or canals, at least one of said canals providing a passageway for feeding or withdrawing fluid, a second canal forming a passageway housing an electrical conductor means connecting the distal end of said device to said circuit which includes said monitor.

8. The apparatus recited in claim 7 wherein said device includes a third canal providing a passageway for a second electrical conductor means connecting a portion of said distal end of said device with said circuit which includes said monitor.

* * * * *